(12) United States Patent
Dorian

(10) Patent No.: US 10,589,193 B2
(45) Date of Patent: Mar. 17, 2020

(54) RED BLOOD CELL ELUTRIATION WASH SYSTEM

(71) Applicant: Randel E. Dorian, San Diego, CA (US)

(72) Inventor: Randel E. Dorian, San Diego, CA (US)

(73) Assignee: Hanuman Medical, San Francisco, CA (US)

( * ) Notice: Subject to any disclaimer, the term of this patent is extended or adjusted under 35 U.S.C. 154(b) by 109 days.

(21) Appl. No.: 15/828,485

(22) Filed: Dec. 1, 2017

(65) Prior Publication Data

US 2018/0154286 A1     Jun. 7, 2018

Related U.S. Application Data

(60) Provisional application No. 62/429,308, filed on Dec. 2, 2016.

(51) Int. Cl.
*B01D 21/26* (2006.01)
*B04B 5/04* (2006.01)
(Continued)

(52) U.S. Cl.
CPC ......... *B01D 21/262* (2013.01); *A61M 1/3696* (2014.02); *B01D 21/0087* (2013.01);
(Continued)

(58) Field of Classification Search
CPC .............. A61M 1/3693; A61M 1/3695; A61M 1/3696; A61M 2202/0429; B04B 1/12; B04B 5/04; B04B 5/0407; B04B 5/0421; B04B 5/0442; B04B 15/12; B04B 2005/0471; B01D 21/0087; B01D 21/262; B01D 2221/10
See application file for complete search history.

(56) References Cited

U.S. PATENT DOCUMENTS 3,080,108 A    3/1963 Jacobson
4,032,122 A *  6/1977 Anders .................. B04B 5/06
                                                   266/169
(Continued)

OTHER PUBLICATIONS

"U.S. Appl. No. 15/828,481, Notice of Allowance dated Apr. 29, 2019", 8 pgs.
(Continued)

*Primary Examiner* — Timothy C Cleveland
(74) *Attorney, Agent, or Firm* — Schwegman Lundberg & Woessner, P.A.

(57) ABSTRACT

A funnel element having an open end and a closed pointed end configured to receive a multi-component fluid containing a solid fraction. The solid fraction can comprise cellular material that sediments toward the closed pointed end to form a cell pack. A wash fluid can be pumped through the cell pack to entrain microparticles and soluble contaminants. The wash fluid can be introduced into the funnel element below the cell pack such that the wash fluid percolates through the cell pack. The percolating wash fluid can dislodge microparticles or other contaminants trapped within the cell pack. Additional wash fluids can be added to funnel element where excess wash fluids overflow from the funnel element through the open end of the funnel element.

14 Claims, 5 Drawing Sheets

(51) Int. Cl.
  *B01D 21/00* (2006.01)
  *B04B 15/12* (2006.01)
  *A61M 1/36* (2006.01)
  *B04B 1/20* (2006.01)

(52) U.S. Cl.
  CPC ............ *B04B 5/0442* (2013.01); *B04B 15/12* (2013.01); *B01D 2221/10* (2013.01); *B04B 1/2016* (2013.01); *B04B 5/0407* (2013.01); *B04B 2005/0471* (2013.01)

(56) References Cited

U.S. PATENT DOCUMENTS

| | | | |
|---|---|---|---|
| 4,854,933 | A | 8/1989 | Mull |
| 6,544,162 | B1 | 4/2003 | Van et al. |
| 8,182,701 | B2 * | 5/2012 | Lake .................. B01D 21/0087 210/207 |
| 8,540,078 | B2 | 9/2013 | Leach et al. |
| 10,406,534 | B2 | 9/2019 | Dorian |
| 2008/0011684 | A1 | 1/2008 | Dorian et al. |
| 2015/0024922 | A1 | 1/2015 | Castillo Gonzalez et al. |
| 2018/0154373 | A1 | 6/2018 | Dorian |
| 2018/0154374 | A1 | 6/2018 | Dorian |

OTHER PUBLICATIONS

"U.S. Appl. No. 15/828,483, Non Final Office Action dated May 14, 2019", 15 pgs.

"U.S. Appl. No. 15/828,483, Final Office Action dated Sep. 11, 2019", 15 pgs.

"U.S. Appl. No. 15/828,483, Response filed Aug. 14, 2019 to Non Final Office Action dated May 14, 2019", 16 pgs.

* cited by examiner

RED BLOOD CELL ELUTRIATION WASH SYSTEM

CLAIM OF PRIORITY

This patent application claims the benefit of priority, under 35 U.S.C. Section 119(e), to Randel E. Dorian, U.S. Patent Application Ser. No. 62/429,308, entitled "RED BLOOD CELL ELUTRIATION WASH SYSTEM," filed on Dec. 2, 2016, each of which is hereby incorporated by reference herein in its entirety.

TECHNICAL FIELD

This document pertains generally, but not by way of limitation, to washing systems for red blood cells and other cellular materials.

BACKGROUND

Whole blood samples are often fractionated to separate red blood cells, platelets, and other cellular materials from the plasma and other fluid components of the whole blood. A selected fraction, typically red blood cells or cellular materials, can be selectively withdrawn from the fractionated whole blood sample for use in certain medical applications. The isolated cellular material is often further processed by adding one or more wash fluids to the isolated cellular materials to remove any plasma or other undesirable fluids or materials clinging to or intermixed with the desired cellular material. The resulting wash fluid comprising cellular material within the wash fluids is often fractionated again to separate and isolate the cellular material from the wash fluids.

For certain medical applications, the cellular materials must often be washed multiple times to cleanse the cellular material to certain predetermined standards. During centrifugation, the cellular material compresses into a bed or pack of cells. Repeated washing can disrupt the cell pack dislodging cellular material, which can become entrained within the wash fluid and discarded with the wash fluid after each wash cycle. However, as the cellular materials are only loosely packed together and not substantially adhered to each other, adding any wash fluid to the cell pack can easily dislodge cells from the cell pack resulting in unnecessary waste.

OVERVIEW

The present inventors have recognized, among other things, that a problem to be solved can include the loss of cellular material from a cell pack while washing cellular material with wash fluids. In an example, the present subject matter can provide a solution to this problem, such as by receiving at least a solid fraction of a multi-component fluid within a funnel element having an open end and a closed pointed end. The solid fraction can comprise cellular material that sediments toward the closed pointed end to form a cell pack. A wash fluid can be pumped through the cell pack to entrain microparticles and soluble contaminants. In an example, the wash fluid can be introduced into the funnel element below the cell pack such that the wash fluid percolates through the cell pack. The percolating wash fluid can dislodge microparticles or other contaminants trapped within the cell pack. Additional wash fluids can be added to funnel element where excess wash fluids overflow from the funnel element through the open end of the funnel element.

In an example, the funnel element can be oriented vertically with the closed pointed end pointed downward such that gravity causes the cellular material within the funnel element to sediment downward toward the closed pointed end at a sedimentation rate. In this configuration, the wash fluids can be pumped through the cell pack at a predetermined flow rate; wherein the predetermined flow rate is less than the sedimentation rate of the cellular material caused by gravity. The continuous supply of wash fluid at the predetermined flow rate can reach an equilibrium with the sedimentation rate. At equilibrium, a loosely packed cell pack is formed at the closed pointed end and a supernatant is formed above the cell pack, wherein the cell pack is separated from the supernatant by a boundary layer. As additional wash fluid is added to the funnel element, the excess wash fluid overflows through the open end of the funnel element gradually removing entrained microparticles and soluble contaminants within the supernatant. With continuous washing, the supernatant will become increasing transparent as entrained microparticles and soluble contaminants are washed from the cellular material and flushed from the funnel element.

In an example, a centrifuge container can comprise an outer housing defining an internal chamber and including a funnel element having an open end and a pointed closed end. The funnel element can be oriented such that during centrifugation when the centrifuge container is rotated around a rotational axis, the pointed end of the funnel element is oriented radially outward from the rotational axis. A solid fraction of a fractionated multi-component fluid can be added to the funnel element or collected within the funnel element during fractionation of the multi-component fluid by centrifugation of the centrifuge container. The centrifugation container can be rotated about the rotational axis to cause the cellular materials to flow toward the pointed end at a sedimentation rate. The centrifuge container can include a wash fluid reservoir for providing wash fluid through the open end of the funnel element to wash the cellular material. The continuous supply of wash fluid from the wash fluid reservoir at the predetermined flow rate can reach an equilibrium with the sedimentation rate created by the rotation of the centrifugation container. Wash fluid can be continuously supplied until the cellular material is sufficiently cleansed of micro-particulates and soluble contaminants.

In an example, a method of washing cellular material fractionated from a multi-component fluid can include collecting the cellular material within a funnel element having an open end and a closed pointed end. The method can include applying a counter force to the cellular material to cause the cellular material to move toward the closed pointed end at a sedimentation rate to form a cell pack. The counter force can be at least one of gravitational force and centrifugal force. The method can further include pumping wash fluid through the open end of the funnel element and creating a counterflow through the cell pack at a predetermined flow rate; wherein the sedimentation rate is sufficiently high to retain cellular material within the funnel element as excess wash fluid overflows from the funnel element.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings generally illustrate, by way of example, but not by way of limitation, various embodiments discussed in the present document.

DETAILED DESCRIPTION

Figure 1:
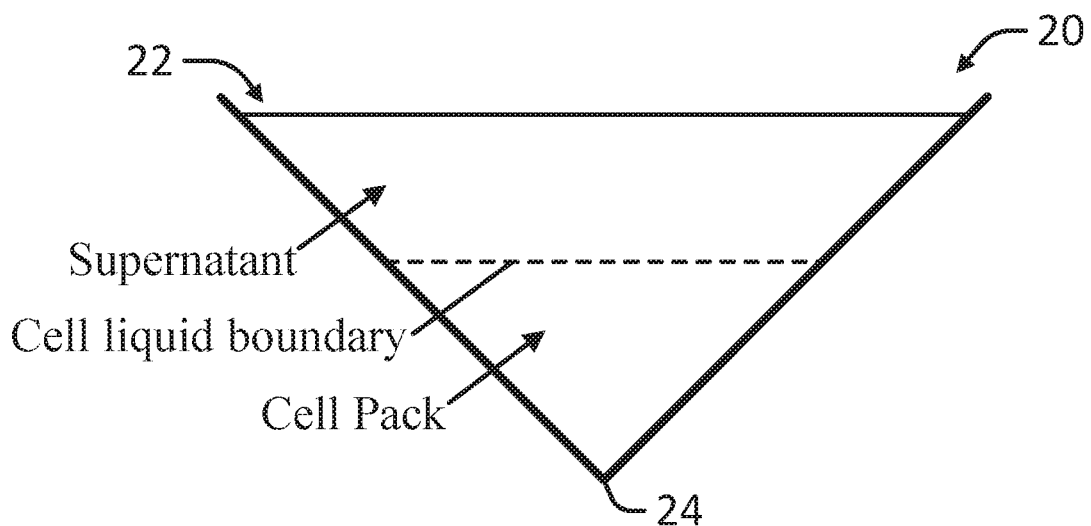
FIG. 1 is a schematic diagram of a multi-component fluid fractionated into a solid fraction and a liquid fraction within a funnel according to an example of the present disclosure.

As depicted in FIGS. 1 and 2, a wash system, according to an example of the present disclosure, can include a funnel element 20 having an open end 22 and a pointed closed end 24. A solid fraction of a multi-component fluid (e.g. red blood cells of a fractionated whole blood) can be received within the funnel element 20. The solid fraction can also be provided as a pre-fractionated multi-component fluid with entrained solids; a liquid fraction and a solid fraction of a fractionated multi-component fluid; an isolated solid fraction from a fractionated multi-component fluid; or a wash solution containing entrained solids. In an example, the funnel element 20 can be centrifuged to fractionate an unfractionated multi-component fluid or a wash solution containing entrained solids to extract the solid fraction. The funnel element 20 can be oriented vertically with the pointed closed end 24 pointed downward such that gravity sediments the solids toward the pointed closed end 24 at a sedimentation rate to form a loosely packed cell pack. In an example, the sedimentation rate caused by gravity can be about 1.0 to about 2.0 microns per second. In certain example, the sedimentation rate caused by gravity can be about 1.5 microns per second.

Figure 2A:
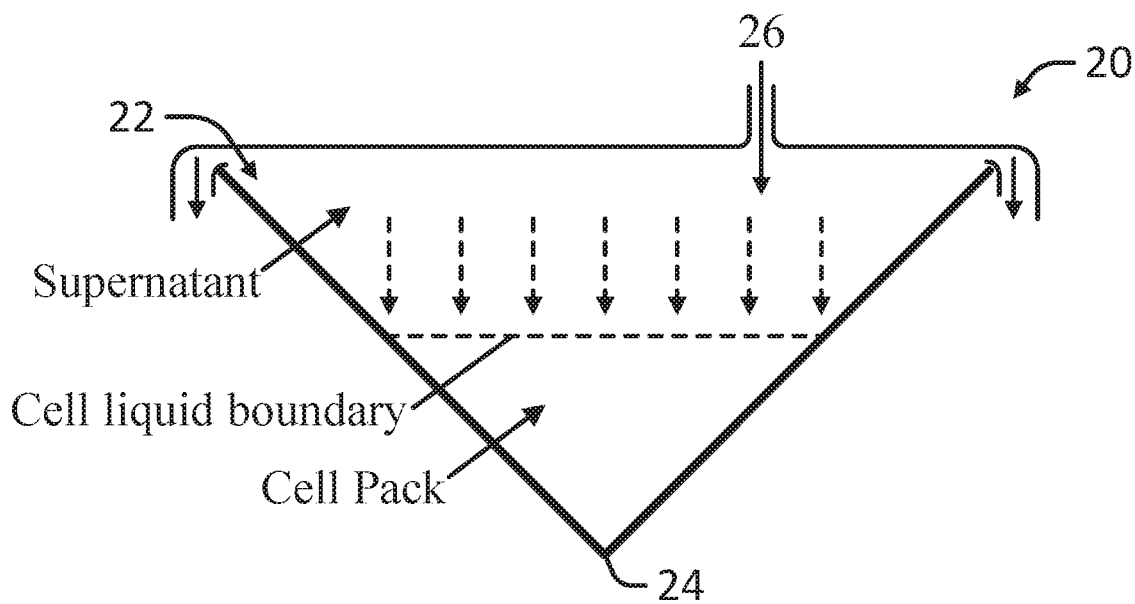
FIG. 2A is a schematic diagram of a multi-component fluid fractionated into a solid component and a liquid component within a funnel during centrifugation with a wash flow being added to the funnel according to an example of the present disclosure.
Figure 2B:
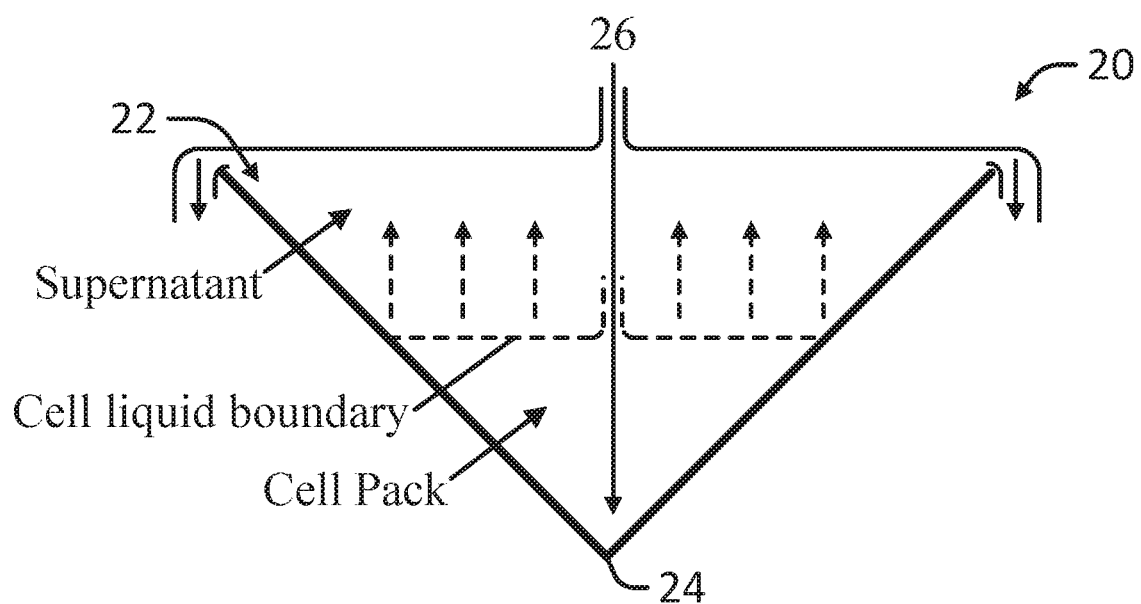
FIG. 2B is a schematic diagram of a multi-component fluid fractionated into a solid component and a liquid component within a funnel during centrifugation with a wash flow being added to the funnel to percolate through a cell pack according to an example of the present disclosure.

As illustrated in FIGS. 2A-B, a wash fluid can be provided at a predetermined flow rate from a wash fluid source 26 through the open end 22 of the funnel element 20 and through the cell pack. As illustrated in FIG. 2A, in an example, the wash fluid can be added over the cell pack. As illustrated in FIG. 2B, in an example, the wash fluid can be provided proximate to the pointed closed end 24 such that the wash fluid percolates through the cell pack. In this configuration, the wash fluid can lightly disrupt the cell pack to dislodge loose microparticulates or other impurities entrained within the cell pack improving capture of the microparticulates or other impurities. The wash fluid can be continuously or intermittently supplied to fill and overflow the funnel element 20 through the open end 22. In an example, the predetermined flow rate can create a counter-flow of wash fluid opposite the sedimentation of the cellular material. In an example, the counterflow can be about 60 to about 70 microliters per minute. In certain examples, the counterflow can be about 65 microliters per minute resulting in a linear flow velocity of about 1.3 microns per second. As the sedimentation rate is greater than the linear flow velocity, gravity is sufficient to retain the cellular material of the solid fraction within the funnel element 20. The wash fluid can be applied continuously at a predetermined flow rate or intermittently to increase the effective sedimentation rate relative to the linear flow velocity to improve sedimentation of the desired solids dislodged from the cell pack by the wash fluids back onto the cell pack.

As illustrated in FIG. 2, in an example, the counterflow of wash fluid can reach an equilibrium with the sedimentation created by gravity resulting in a supernatant over a loosely packed cell pack, wherein the supernatant is separated from the cell pack by a boundary layer. In certain examples, the solid fraction can initially have a hematocrit of about 90% where the hematocrit of the cell pack can be about 80% at equilibrium. The supernatant can include entrained microparticulates and dissolved soluble contaminants, which can decrease the transparency of the supernatant. As the cell pack is repeatedly or continually washed, the supernatant will become increasingly transparent as entrained microparticulates and dissolved soluble contaminants are removed from the cell pack and flushed with excess wash fluid. The wash solution can be provided until the supernatant reaches a predetermined transparency corresponding to a desired cleanliness of the cell pack.

Figure 3:
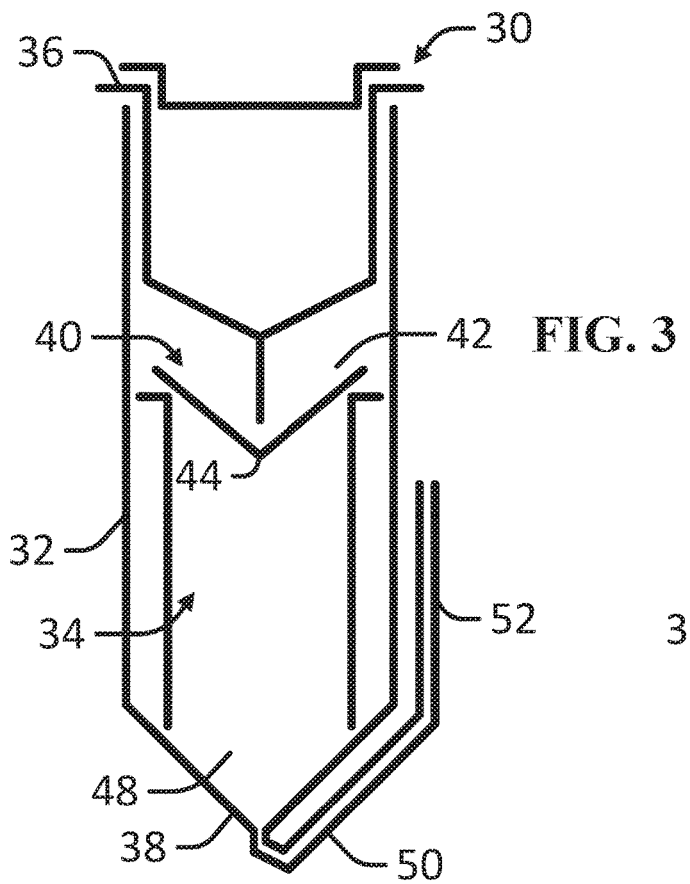
FIG. 3 is a schematic diagram of a separation container for washing a solid fraction of a multi-component fluid according to an example of the present disclosure.
Figure 4:
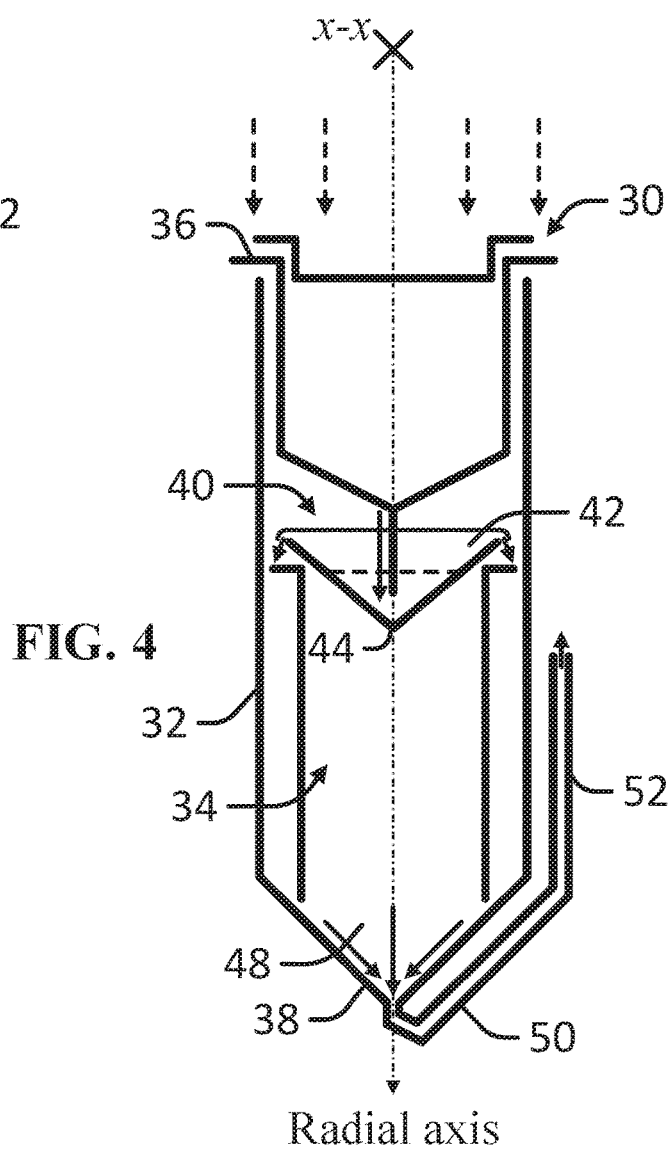
FIG. 4 is a schematic diagram of a separation container for washing a solid fraction of a multi-component fluid during centrifugation and with a wash flow according to an example of the present disclosure.

As depicted in FIGS. 3 and 4, a centrifuge container 30, according to an example of the present disclosure, can include an outer housing 32 defining an internal chamber 34, the outer housing 32 having an open top end 36 and a bottom end 38. A funnel element 40 having an open end 42 and a pointed closed end 44 can be positioned within the internal chamber 34 of the outer housing 32. A solid fraction of a multi-component fluid (e.g. red blood cells of a fractionated whole blood) can be fed through the open top end 36 into the outer housing 32 and received within the funnel element 36. The solid fraction can also be provided as a pre-fractionated multi-component fluid with entrained solids; a liquid fraction and a solid fraction of a fractionated multi-component fluid; an isolated solid fraction from a fractionated multi-component fluid; or a wash solution containing entrained solids. In an example, the centrifuge container 30 can be centrifuged to fractionate an unfractionated multi-component fluid or a wash solution containing entrained solids to extract the solid fraction and capture at least the solid fraction within the funnel element 40.

As illustrated in FIGS. 3 and 4, the centrifuge container 30 can be rotatable about a rotational axis x-x, where the pointed closed end 44 is pointed radially outward from the rotational axis x-x. In this configuration, the continued rotation of the centrifuge container 30 can push the solid fraction toward the pointed closed end 44 of the funnel element 40 at a sedimentation rate to form a cell pack at the pointed closed end 44. The centrifuge container 30 can include a wash fluid reservoir configured to provide wash fluids at a predetermined flowrate through the open end 42 of the funnel element 40 during centrifugation of the centrifuge container 30. The wash fluid can intermix with the cell pack of the solid fraction. The wash fluid flowrate can create a linear flow velocity within the funnel element 40 counter to the centrifugal forces created by the rotation of centrifuge container 30. The centrifuge container 30 can be rotated to increase the centrifugal force applied the solid fraction and correspondingly the sedimentation rate to correspond to the linear flow velocity, wherein the sedimentation rate is greater than the linear flow velocity to retain cellular material within the funnel element 40 during washing.

The wash fluid can be continuously or intermittently supplied to fill and overflow the funnel element 40. Excess wash fluid can overflow from the funnel element 40 through the open end 42, while the orientation of the funnel element 40 allows continued rotation of the centrifuge container 30 retains the solid fraction within the funnel element 40. The wash fluid can be applied continuously at a predetermined flow rate or intermittently to allow desired solids dislodged from the cell pack by the wash fluids to resettle on the cell pack.

As depicted in FIGS. 3-4, in an example, the centrifuge container 30 can include a fluid trap 48 at the bottom end 38 of the outer housing 32 for collecting excess wash fluids overflowing from the funnel element 40. The outer housing 32 can include a withdrawal outlet 50 through the bottom end 38 of the outer housing 32. In an example, a sight tube 52 can be coupled to the withdrawal outlet 50. The sight tube 52 can be positioned parallel to the outer housing 32 and transparent to permit visual evaluation of the wash fluids within the fluid trap 48 at the bottom end 38.

Figure 5:
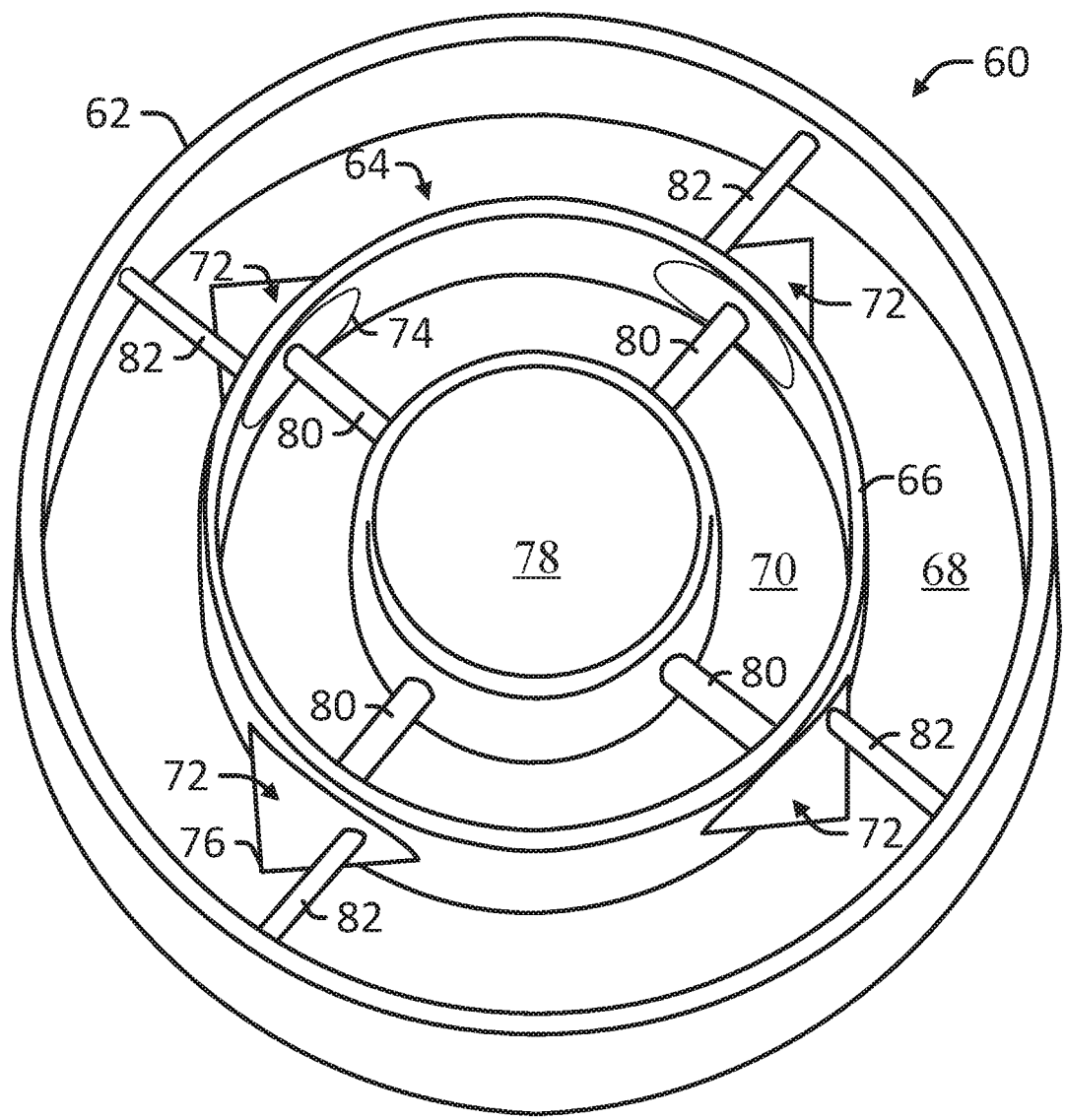
FIG. 5 is a perspective view of a rotor for washing a solid fraction of a multi-component fluid according to an example of the present disclosure.
Figure 6:
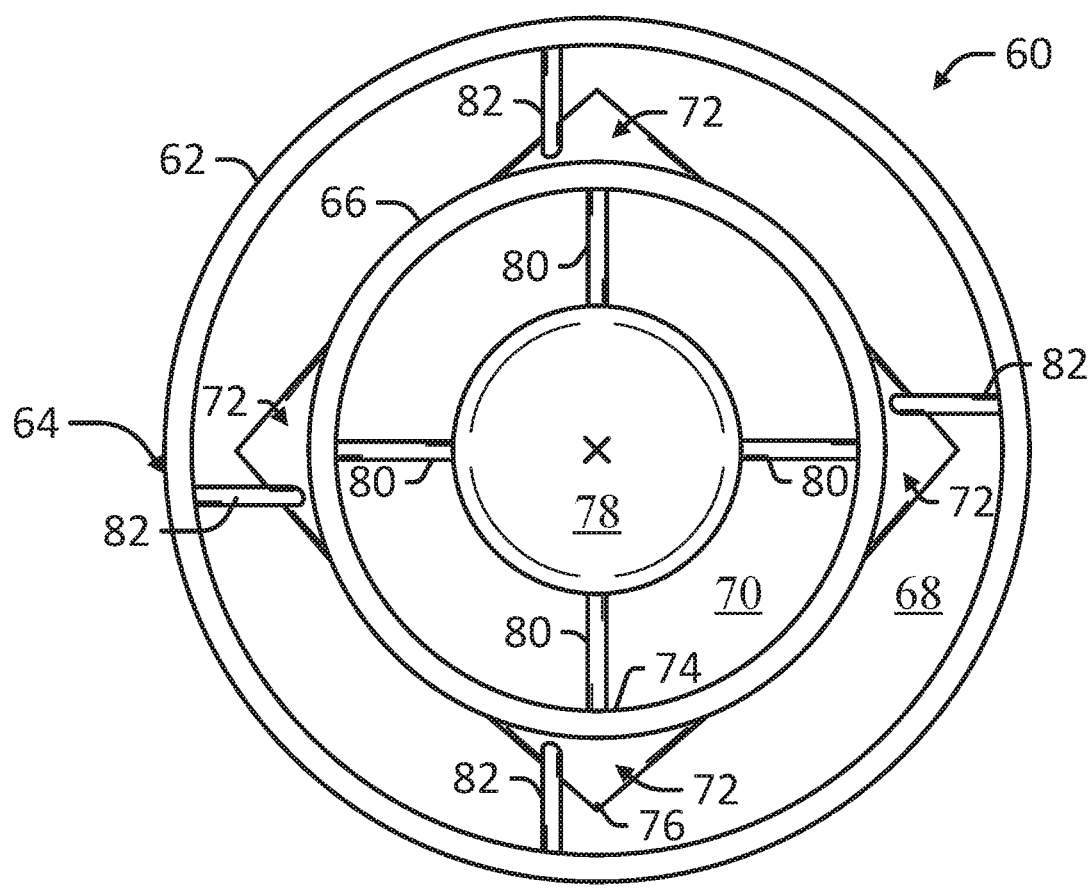
FIG. 6 is a top view of a rotor for washing a solid fraction of a multi-component fluid according to an example of the present disclosure.

As depicted in FIGS. 5 and 6, a rotor 60, according to an example of the present disclosure, can include an outer housing 62 defining an inner chamber 64, wherein the inner chamber 64 is divided by an inner wall 66 into an outer portion 68 and an inner portion 70. At least one funnel element 72 can be positioned circumferentially around the inner wall 66. Each funnel element 72 can have an open end 74 and a pointed closed end 76, wherein the open end 74 is oriented toward the inner portion 70 to receive solids and fluids from the inner portion 70 of the inner chamber 64 when the rotor 60 rotates about a rotational axis y-y. In this configuration, the funnel element 72 can be positioned within the outer portion 68 such that the pointed closed end 76 is pointed radially outward from the rotational axis y-y as illustrated in FIG. 6.

A solid fraction of a multi-component fluid (e.g. red blood cells of a fractionated whole blood) can be positioned within the inner portion 70 of inner chamber 64. The solid fraction can be provided as a pre-fractionated multi-component fluid with entrained solids, a liquid fraction and a solid fraction of a fractionated multi-component fluid; an isolated solid fraction from a fractionated multi-component fluid; or a wash solution containing entrained solids. The rotor 60 can be rotated about rotational axis y-y to force the contents of the inner portion 70 of the inner chamber 64 against the inner wall 66 and into the funnel elements 72.

In an example, the rotor 60 can include wash fluid reservoir 78 centered on the rotational axis y-y and operably connected to each funnel element 72 by a supply line 80. In operation, rotation of the rotor 60 can cause wash fluid from the wash fluid reservoir 78 to move radially outward from the wash fluid reservoir 78 into the corresponding funnel element 72. The wash fluid can intermix with the cell pack of the solid fraction. The wash fluid can be continuously or intermittently supplied to fill and overflow from the funnel element 40 through a corresponding waste line 82 proximate to the open end 74 of the funnel element 72. The waste line 82 permits continued rotation of the rotor 60 to retain the solid fraction within each corresponding funnel element 72. The wash fluid can be applied continuously at a predetermined flow rate or intermittently to allow desired solids that are dislodged from the cell pack by the wash fluids to resettle on the cell pack.

VARIOUS NOTES & EXAMPLES

Example 1 is a wash system for washing cellular material, comprising: a funnel element for receiving a multi-component fluid containing cellular material, the funnel element having an open end and a pointed closed end, wherein the funnel element is configured to cause the cellular material to settle at the pointed closed end at a sedimentation rate; and a wash fluid reservoir configured to supply a wash fluid to the funnel element at a predetermined flow rate such that excess wash fluids overflow through the open end of the funnel element, thereby creating a counterflow of cellular material toward the open end, wherein the counterflow is less than the sedimentation rate such that the cellular material is retained within the funnel element.

In Example 2, the subject matter of Example 1 optionally includes wherein the pointed closed end is oriented downward such that gravity causes the cellular material to settle toward the pointed closed end.

In Example 3, the subject matter of any one or more of Examples 1-2 optionally include wherein the funnel element is rotatable about a rotational axis with the pointed closed end being pointed radially outward such that rotation of the funnel element causes the cellular material to move outward toward the pointed closed end.

In Example 4, the subject matter of any one or more of Examples 1-3 optionally include microns per second.

In Example 5, the subject matter of Example 4 optionally includes microns per second.

In Example 6, the subject matter of any one or more of Examples 1-5 optionally include a fluid trap positioned to capture wash fluid overflowing from the open end of the funnel element.

In Example 7, the subject matter of Example 6 optionally includes wherein the fluid trap further comprises: a withdrawal outlet for removing overflowing wash fluid from the fluid trap.

In Example 8, the subject matter of Example 7 optionally includes wherein a sight tube is fluidly connected to the withdrawal outlet.

Example 9 is a centrifuge container for washing cellular material, comprising: a funnel element for receiving a multi-component fluid containing cellular material, the funnel element having an open end and a pointed closed end; and a wash fluid reservoir configured to supply a wash fluid to the funnel element at a predetermined flow rate such that excess wash fluids overflow through the open end of the funnel element, thereby creating a counterflow of cellular material toward the open end; wherein the centrifuge container is rotatable about a rotational axis with the pointed closed end is oriented radially outward from the rotational axis such that cellular material is pushed toward the closed pointed end, wherein the counterflow is less than the sedimentation rate such that the cellular material is retained within the funnel element.

In Example 10, the subject matter of Example 9 optionally includes microns per second.

In Example 11, the subject matter of Example 10 optionally includes microns per second.

In Example 12, the subject matter of any one or more of Examples 9-11 optionally include a fluid trap positioned to capture wash fluid overflowing from the open end of the funnel element.

In Example 13, the subject matter of Example 12 optionally includes wherein the fluid trap further comprises: a withdrawal outlet for removing overflowing wash fluid from the fluid trap.

In Example 14, the subject matter of Example 13 optionally includes wherein a sight tube is fluidly connected to the withdrawal outlet.

Example 15 is a rotor for washing cellular material, comprising: an outer housing defining an inner chamber and including an inner wall, the inner wall dividing the inner chamber into an inner portion and an outer portion, wherein the inner portion is configured to receive a multi-component containing cellular materials; at least one funnel element positioned circumferentially around the inner wall, each funnel element having an open end and a pointed closed end; and a wash fluid reservoir positioned in the inner portion configured to supply a wash fluid to the funnel element; wherein the rotor is rotatable about a rotational axis centered in the inner portion such that cellular materials are directed into the open end of the funnel element and collect at the closed end of the funnel element; and wherein rotation of the rotor draws wash fluids from the wash fluid reservoir into funnel element.

In Example 16, the subject matter of Example 15 optionally includes wherein the wash fluid reservoir is fluidly connected to each funnel element with a supply line.

In Example 17, the subject matter of any one or more of Examples 15-16 optionally include wherein each funnel element further includes at least one waste line for capturing excess wash fluids.

Example 18 is a method of washing cellular material, comprising: providing a multi-component fluid containing a cellular material within a funnel element having an open end and a pointed closed end; rotating the funnel element about a rotational axis to cause the cellular material to settle at the pointed closed end at a sedimentation rate; and supplying a wash fluid to the fluid element at a predetermined flow rate such that excess wash fluids overflow through the open end of the funnel element and create a counterflow of cellular material toward the open end; wherein the counterflow is less than the sedimentation rate such that the cellular material is retained within the funnel element.

In Example 19, the subject matter of Example 18 optionally includes monitoring an opacity of the overflowing wash fluids; and stopping the supply of wash fluids when the opacity of the wash fluid reaches a predetermined transparency.

Each of these non-limiting examples can stand on its own or can be combined in any permutation or combination with any one or more of the other examples.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. A wash system for washing cellular material, comprising:
   a funnel element for receiving a multi-component fluid containing cellular material, the funnel element having an open end and a pointed closed end, wherein the funnel element is configured to cause the cellular material to settle at the pointed closed end at a sedimentation rate; and
   a wash fluid reservoir configured to supply a wash fluid to the funnel element at a predetermined flow rate such that excess wash fluids overflow through the open end of the funnel element, thereby creating a counterflow of cellular material toward the open end;
   wherein the counterflow is less than the sedimentation rate such that the cellular material is retained within the funnel element.

2. The wash system of claim 1, wherein the pointed closed end is oriented downward such that gravity causes the cellular material to settle toward the pointed closed end.

3. The wash system of claim 1, wherein the funnel element is rotatable about a rotational axis with the pointed closed end being pointed radially outward such that rotation of the funnel element causes the cellular material to move outward toward the pointed closed end.

4. The wash system of claim 1, wherein the sedimentation rate is between about 1.0 to about 2.0 microns per second.

5. The wash system of claim 4, wherein the predetermined flow rate is about 60 to about 70 microliters and the counterflow is about 1.3 microns per second.

6. The wash system of claim 1, further comprising a fluid trap positioned to capture wash fluid overflowing from the open end of the funnel element.

7. The wash system of claim 6, wherein the fluid trap further comprises:
   a withdrawal outlet for removing overflowing wash fluid from the fluid trap.

8. The wash system of claim 7, wherein a sight tube is fluidly connected to the withdrawal outlet.

9. A centrifuge container for washing cellular material, comprising:
   a funnel element for receiving a multi-component fluid containing cellular material, the funnel element having an open end and a pointed closed end; and
   a wash fluid reservoir configured to supply a wash fluid to the funnel element at a predetermined flow rate such that excess wash fluids overflow through the open end of the funnel element, thereby creating a counterflow of cellular material toward the open end;
   wherein the centrifuge container is rotatable about a rotational axis with the pointed closed end is oriented radially outward from the rotational axis such that cellular material is pushed toward the closed pointed end,
   wherein the counterflow is less than the sedimentation rate such that the cellular material is retained within the funnel element.

10. The centrifuge container of claim 9, wherein the sedimentation rate is between about 1.0 to about 2.0 microns per second.

11. The centrifuge container of claim 10, wherein the predetermined flow rate is about 60 to about 70 microliters and the counterflow is about 1.3 microns per second.

12. The centrifuge container of claim 9, further comprising a fluid trap positioned to capture wash fluid overflowing from the open end of the funnel element.

13. The centrifuge container of claim 12, wherein the fluid trap further comprises:
   a withdrawal outlet for removing overflowing wash fluid from the fluid trap.

14. The centrifuge container of claim 13, wherein a sight tube is fluidly connected to the withdrawal outlet.

* * * * *